(12) United States Patent
Hammerschmidt et al.

(10) Patent No.: US 11,169,103 B2
(45) Date of Patent: Nov. 9, 2021

(54) THERMAL GAS SENSOR, METHOD FOR MEASURING THE THERMAL DIFFUSIVITY OF A GAS OR GAS MIXTURE AND METHOD FOR MEASURING THE THERMAL CONDUCTIVITY OF A GAS OR GAS MIXTURE

(71) Applicant: DIEHL METERING GMBH, Ansbach (DE)

(72) Inventors: Ulf Hammerschmidt, Braunschweig (DE); Andreas Benkert, Ansbach (DE); Christoph Sosna, Nuremberg (DE); Karl Herrmann, Eckental (DE)

(73) Assignee: Diehl Metering GmbH, Ansbach (DE)

( * ) Notice: Subject to any disclaimer, the term of this patent is extended or adjusted under 35 U.S.C. 154(b) by 100 days.

(21) Appl. No.: 16/654,234

(22) Filed: Oct. 16, 2019

(65) Prior Publication Data
US 2020/0124549 A1  Apr. 23, 2020

(30) Foreign Application Priority Data
Oct. 19, 2018 (DE) .......................... 102018008286.6

(51) Int. Cl.
*G01N 25/18* (2006.01)
*G01N 25/00* (2006.01)
*G01K 7/00* (2006.01)

(52) U.S. Cl.
CPC .................................. *G01N 25/18* (2013.01)

(58) Field of Classification Search
USPC .................................... 374/43, 44, 183, 208
See application file for complete search history.

(56) References Cited

U.S. PATENT DOCUMENTS

| 4,944,035 A | 7/1990 | Aagard et al. |
| 6,159,386 A * | 12/2000 | Wienand ............... H01C 7/008 |
| | | 216/16 |
| 6,169,965 B1 | 1/2001 | Kubisiak et al. |

(Continued)

FOREIGN PATENT DOCUMENTS

| DE | 68927242 T2 | 12/1989 |
| DE | 102014008284 A1 | 12/2015 |

(Continued)

OTHER PUBLICATIONS

Kliche, et al.: "Sensor for Thermal Gas Analysis Based on Micromachined Silicon-Microwires"—IEEE Sensors Journal, vol. 13, No. 7, Jul. 2013, pp. 2626-2635.

*Primary Examiner* — Mirellys Jagan
(74) *Attorney, Agent, or Firm* — Laurence A. Greenberg; Werner H. Stemer; Ralph E. Locher

(57) ABSTRACT

A thermal gas sensor for measuring the thermal diffusivity and/or the thermal conductivity of a gas or gas mixture includes a substrate. In the surface of the substrate a trench is formed, as well as at least two conductor structures arranged at a distance from one another on the surface of the substrate. The conductor structures respectively each contain at least two contact sections and a web section connected to the contact sections, the web sections of the conductor structures crossing over the trench at a distance from one another. At least one slot is formed between at least two contact sections of different conductor structures in at least one region of the surface of the substrate.

12 Claims, 2 Drawing Sheets

(56) References Cited

U.S. PATENT DOCUMENTS

| | | | |
|---|---|---|---|
| 2010/0284002 A1* | 11/2010 | Li | G01N 25/18 356/301 |
| 2013/0209315 A1 | 8/2013 | Kimura | |
| 2014/0138259 A1 | 5/2014 | Mickelson et al. | |
| 2017/0097314 A1 | 4/2017 | Christenson et al. | |
| 2017/0102256 A1 | 4/2017 | Sosna et al. | |
| 2020/0072773 A1 | 3/2020 | Hammerschmidt et al. | |
| 2020/0209174 A1* | 7/2020 | Alexeenko | G01N 25/00 |

FOREIGN PATENT DOCUMENTS

| | | |
|---|---|---|
| DE | 102018006868 A1 | 3/2020 |
| EP | 0348245 B1 | 12/1989 |
| EP | 3153851 A1 | 4/2017 |
| WO | 9934198 A1 | 7/1999 |

\* cited by examiner

THERMAL GAS SENSOR, METHOD FOR MEASURING THE THERMAL DIFFUSIVITY OF A GAS OR GAS MIXTURE AND METHOD FOR MEASURING THE THERMAL CONDUCTIVITY OF A GAS OR GAS MIXTURE

CROSS-REFERENCE TO RELATED APPLICATION

This application claims the priority, under 35 U.S.C. § 119, of German application DE 10 2018 008 286.6, filed Oct. 19, 2018; the prior application is herewith incorporated by reference in its entirety.

BACKGROUND OF THE INVENTION

Field of the Invention

The invention relates to a thermal gas sensor for measuring the thermal diffusivity and/or the thermal conductivity of a gas or gas mixture, containing a substrate, in the surface of which a trench is formed, as well as at least two conductor structures arranged at a distance from one another on the surface of the substrate. The conductor structures respectively contain at least two contact sections and a web section connected to these contact sections. The web sections of the conductor structures crossing over the trench at a distance from one another. The invention furthermore relates to a method for measuring the thermal diffusivity of a gas or gas mixture as well as to a method for measuring the thermal conductivity of a gas or gas mixture.

Such a thermal gas sensor may, for example, be used in order to determine the thermal diffusivity of natural gases. To this end, a heat flux flowing through the gas or gas mixture to be studied is generated between the conductor structures. The thermal diffusivity of the gas or gas mixture may be deduced by the time taken for heat propagation between the conductor structures. Parasitic heat flux, i.e. heat flows which do not propagate through the gas to be studied, but for example flow through the substrate, in this case represent a problem. Such heat flows vitiate the measurement result, or necessitate elaborate adaptations of the mathematical model used in order to determine the thermal diffusivity of the gas. This also applies similarly during the measurement of a thermal conductivity of a gas or a gas mixture with the aid of such a thermal gas sensor.

SUMMARY OF THE INVENTION

The object of the invention is therefore to provide an improved thermal gas sensor which avoids or reduces parasitic heat flows.

In order to achieve this object, according to the invention at least one slot is formed between at least two contact sections of different conductor structures in at least one region of the surface of the substrate.

By the slot provided between the contact sections of different conductor structures, the solid-state bridge existing between the contact sections through the substrate of the thermal gas sensor is partially broken. This offers the advantage that a parasitic heat flux flowing through the substrate between the at least two conductor structures is avoided or at least reduced. By the avoidance or reduction of this parasitic heat flux, more accurate and simple determination of thermal diffusivity and/or thermal conductivity of the gas or gas mixture by the thermal gas sensor is possible.

The at least two contact sections of the conductor structures are located in particular on the two sides of the trench and are connected to the web section of the conductor structure which crosses over the trench, particularly in a self-supporting fashion. The at least two conductor structures of the thermal gas sensor are arranged on the surface of the substrate in such a way that their web sections cross over the trench at a distance from one another. In order to measure the thermal diffusivity of a gas or gas mixture flowing around the web sections, a thermal time of flight of a heat flux between a web section, operated as a heating element, of a conductor structure and a web section, operated as a temperature sensor, of a further conductor structure is measured. The better the gas surrounding the web sections transports heat, the faster the temperature rise generated by the heating element reaches the temperature sensor. The time, or time of flight, until the temperature of the temperature sensor rises to its maximum forms a measure of the thermal diffusivity of the gas. The conductor structures with the web elements used as a temperature sensor may, for example, be operated as a resistance thermometer.

Between the contact sections of two neighboring conductor structures, in particular at least one slot may respectively be provided in order to reduce or prevent the parasitic heat flux through the substrate in the region of the surface of the substrate between the at least two contact sections of the neighboring conductor structures. In particular, provision may be made for one or more slots to be provided between a plurality or all of the contact sections of some or all of the conductor structures between the respective neighboring contact sections, so that overall there is only a small, and in particular negligible, heat flux through the substrate.

According to the invention, the trench may extend along a longitudinal direction, the web sections of the conductor structures crossing over the trench parallel or essentially parallel to a transverse direction. The web sections of the conductor structures are consequently arranged offset from one another along the longitudinal direction. With respect to a conductor structure having a web section operated as a heating element, further conductor structures may be arranged in such a way that their web sections cross over the trench at different distances from the heating element. It is also possible that, in the case of a plurality of further conductor structures, these are arranged before and after the web element used as a heating element, in relation to the longitudinal direction of the extent of the trench.

For the trench, according to the invention it may comprise a bottom, which in particular is parallel or essentially parallel to the surface of the substrate, as well as at least two walls, the walls extending between the surface of the substrate and the bottom of the trench, the at least one slot extending from the upper side of the substrate to the bottom of the trench, and/or the at least one slot extending through a wall of the trench. The trench may have a square, rectangular or trapezoidal cross section. The at least one slot may extend from the trench through the region of the surface of the substrate between the two contact sections of neighboring conductor structures. It is of course possible that, in the case of contact structures which are arranged on the surface of the substrate on the two sides of the trench, at least one slot is respectively also made through both walls of the trench. The slot may, at least in sections, extend orthogonally to the wall of the trench, or to the direction in which the trench runs.

According to the invention, the slot may comprise one or more straight sections following on from one another, the slot fully or partially cutting into the region of the surface of the substrate between the at least two contact sections. In this case, provision may be made that the slot, at least in sections, follows the contour, or the edge geometry, of one or both of the contact sections. Preferably, the slot extends essentially centrally between two contact sections of neighboring conductor structures. A plurality of straight sections of a slot, which follow on from one another, may meet one another at different angles so that, as a function of a shape of the contact sections, the slot may extend in different geometries optionally adapted in sections to the shape of one or more neighboring contact sections.

In order to manufacture the trench and/or the slot, according to the invention the trench and/or the at least one slot may be made by etching of the substrate in regions. The etching may in this case, for example, be carried out as wet chemical etching and/or as dry etching.

According to the invention, the slot may have a width of between 1 µm and 50 µm, in particular between 10 µm and 20 µm, and/or in that the trench may have a width of between 0.5 mm and 5 mm and/or a depth of between 100 µm and 500 µm. The width of the slot is in this case independent of the width and/or the depth of the trench. For the manufacturing process, it may prove advantageous for the at least one slot to have the same depth as the trench, although it is also possible for the slot to be deeper or less deep than the trench and/or when there are a plurality of slots, for their depths and/or their widths to differ.

In one preferred configuration of the invention, it is possible that, via the at least two contact sections, the conductor structures can be energized in order to energize the web sections of the conductor structure and/or can be contacted in order to measure a resistance of the web sections, at least one of the conductor structures containing two further contact sections in order to measure a potential drop across the web section. For a conductor structure whose web section is used as a heating element during operation of the thermal gas sensor, two contact sections are sufficient for energizing the web section. For the further conductor structures, which are for example used as a resistance thermometer during operation of the thermal gas sensor, in principle two contact sections are likewise sufficient for measuring the resistance of the web section. For accurate determination of the resistance of a web section of a conductor structure used as a resistance thermometer, for calibration purposes it may, however, be advantageous for these conductor structures to comprise four contact sections, two of which are respectively arranged on one side of the trench on the surface of the substrate. The provision of four contact sections on these conductor structures makes it possible to carry out a four-point measurement on the conductor structures in order to determine the resistance of the web section. For operation of the thermal gas sensor, i.e. for measurement of the thermal diffusivity and/or the thermal conductivity of a gas or gas mixture flowing around the web sections, however, it is sufficient for a resistance measurement of the web section to be carried out by means of two contacts. In order to energize the conductor structures, or in order to measure the electrical resistances of the conductor structures and in particular the web sections, contact means, for example measuring needles and/or bond contacts, may be applied onto the contact sections of the conductor structures in order to carry a connection of the thermal gas sensor to a control device usable for control and measurement and/or to corresponding measuring instruments.

According to the invention, a conductor structure which forms a resistance thermometer and has four contact sections may respectively be arranged on the surface of the substrate, on two opposite sides of a conductor structure which forms a heating element and has two contact sections, a slot being formed between the contact sections of the heating element and respectively at least one contact section of the resistance thermometer. A measurement may in this case be carried out by means of heat propagation in two oppositely extending directions of the longitudinal direction of the trench. In addition to the slots between the contact sections of the conductor structure forming a heating element and the neighboringly arranged conductor structures respectively forming a resistance thermometer, slots between the respective contact sections may of course also be provided between further conductor structures respectively used as a resistance thermometer.

According to the invention, the conductor structures may consist at least partially of nickel, and/or in that the substrate consists at least partially of silicon and/or silicon nitride. A nickel layer, from which the conductor structures are formed, may in this case be between 50 nm and 300 nm, in particular about 200 nm thick. As the substrate, it is for example possible to use silicon which is coated on the surface with silicon nitride, on which the conductor structures are applied. By the silicon nitride, an insulating surface of the substrate is provided, so that no or only a negligible flow of current occurs between the respective conductor structures.

For a method according to the invention for measuring the thermal diffusivity of a gas or gas mixture by a thermal gas sensor according to the invention, provision is made for it to contain the following steps of:

a) provision of the thermal gas sensor and the gas or gas mixture,
b) application of a time-limited current pulse to a conductor structure,
c) time-dependent measurement of the electrical resistance of at least one further conductor structure, and
d) determination of the thermal diffusivity from the time-dependent measurement of the electrical resistance of the at least one further conductor structure and the distance of the web sections of the conductor structures from one another.

The thermal gas sensor may, for example, be connected to a measuring device configured for carrying out the method, for example a microcontroller or the like. It is of course possible for more than one conductor structure to be used as a resistance thermometer, in which case the web sections of these conductor structures may, in particular, be located at different distances and/or in different directions from the web section used as a heating element.

For a method according to the invention for measuring the thermal conductivity of a gas or gas mixture by a thermal gas sensor according to the invention, which contains at least three conductor structures arranged at a distance from one another on the surface of the substrate, provision is made for it to comprise the steps of:

a) provision of the thermal gas sensor and the gas or gas mixture,
b) application of a time-limited current pulse to a conductor structure in order to heat this conductor structure,
c) measurement of temperature values by means of the at least two further conductor structures, and
d) determination of the thermal conductivity from temperature values of the at least two further conductor structures as well as the distance of the web sections of the two further conductor structures from the web section of the heated conductor.

The thermal gas sensor may, for example, be connected to a measuring device configured for carrying out the method, for example a microcontroller or the like. It is of course possible for more than two conductor structures to be used as a resistance thermometer, in which case the web sections of these conductor structures may, in particular, be located at different distances and/or in different directions from the web section used as a heating element. The at least two further conductor structures may be operated as a resistance thermometer, the resistance of the web section, which is proportional to the temperature of the web section, being used as a temperature value. In addition or as an alternative thereto, a current through the web section with constant voltage or a voltage drop across the web section with constant current may also be used as a temperature value. The temperature of the web section operated as a heating element may also be determined by a corresponding resistance measurement.

From the temperature values of the further conductor structures, parameters may subsequently be calculated which parameterize a best-fit line that describes the relationship between the logarithm of the distance of the respective web section of a further conductor structure from the web section of the heated conductor structure and the temperature measurement value. The thermal conductivity of the gas or gas mixture may subsequently be determined from the parameters. Because of the at least one slot between at least two of the conductor structures, parasitic heat flux through the substrate is reduced or prevented, so that a more accurate determination of the thermal conductivity of the gas or gas mixture is possible.

The use of a current pulse for the heating has the advantage that constant heating of the structures of the gas sensor, for example the substrate, is avoided, so that the thermal conductivity can be determined more accurately. For the determination of the thermal conductivity, reference is made to German patent application DE 10 2018 006 868.5, in which determination of the thermal conductivity from the parameters is explained in more detail.

Other features which are considered as characteristic for the invention are set forth in the appended claims.

Although the invention is illustrated and described herein as embodied in a thermal gas sensor, a method for measuring the thermal diffusivity of a gas or a gas mixture and a method for measuring the thermal conductivity of a gas or gas mixture, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
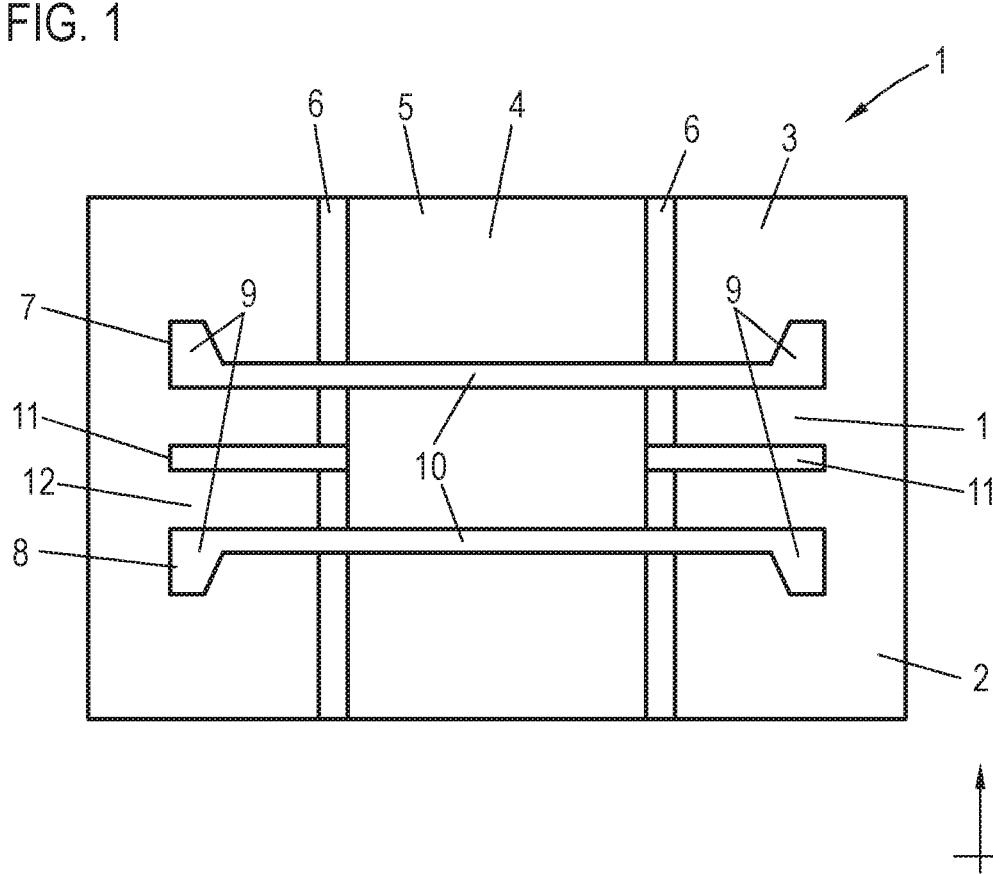
FIG. 1 is a diagrammatic, plan view of a first exemplary embodiment of a thermal gas sensor according to the invention.

Referring now to the figures of the drawings in detail and first, particularly to FIG. 1 thereof, there is shown a schematic plan view of a first exemplary embodiment of a thermal gas sensor 1 according to the invention. The gas sensor 1 has a substrate 2, in a surface 3 of which a trench 4 is formed. The trench 4 has a bottom, which is essentially parallel to the surface 3 of the substrate 2, as well as two walls 6 which connect the bottom 5 to the surface 3 of the substrate 2. In this exemplary embodiment, the trench 4 has a trapezoidal cross section which can be seen from the perspective representation of the first exemplary embodiment in FIG. 2. FIG. 1 furthermore represents two conductor structures 7, 8, which respectively contain two contact sections 9 as well as a web section 10. A web section 10 in this case refers to the part of the conductor structure 9 which crosses over the trench 4. On both sides of the trench, the web section 10 crossing over the trench 4 is respectively adjoined by a contact section 7 of the respective conductor structure 9. Between the neighboring contact sections 9 of the conductor structures 7, 8, a slot 11 is respectively provided on the two sides of the trench 7. The slot 11 extends in a region 12 of the surface 3 of the substrate 2 between the respective contact sections 9 of the neighboring conductor structures 7, 8.

The slot 11 in this case extends respectively through a wall 6 of the trench 4 in a direction transverse to the trench 4, here in the positive or negative X direction corresponding to the extent of the conductor structures 7, 8. It is of course possible for the slot 11 to have a small or even greater extent than the conductor structures 7, 8 in the positive or negative X direction.

By the slot 11, a parasitic heat flux through the substrate 2 is prevented or reduced at least in regions between the contact sections 9 of the conductor structures 7, 8. During the measurement of the thermal diffusivity and/or the thermal conductivity of a gas or gas mixture flowing around the web sections 10 of the gas sensor 1, in this exemplary embodiment, for example, the conductor structure 7 is at least briefly energized via its contact sections 9 so that the web section 10 of the conductor structure 7 is heated. The heat given off by the heated web section 10 of the conductor structure 7 propagates as a function of the thermal diffusivity of the gas or gas mixture flowing around the web sections 10, so that after a certain time, depending on the distance of the web sections 10 from one another, it reaches the web section 10 of the conductor structure 8 and subsequently heats it. The heating of the web section 10 of the conductor structure 7 leads to a change in the electrical resistance of the web section 10 of the conductor structure 8, the resistance change resulting therefrom being measurable via the contact sections 9 of the conductor structure 8. By a time-dependent measurement of the resistance of the web section 10 of the conductor structure 8, while taking into account the distance of the web sections 10 from one another, it is therefore possible to deduce the thermal diffusivity of the gas or gas mixture surrounding the web sections 10. The reduction, resulting from the slot 11, of the parasitic heat fluxes on both sides of the trench between the contact sections 9 of the conductor structures 7, 8 consequently improves the functionality of the sensor, since propagation of heat not propagating through the gas or gas mixture between the conductor structures 7, 8 is prevented or reduced so that measurement can be carried out more accurately and/or with a simpler mathematical model for describing the heat propagation.

Figure 2:
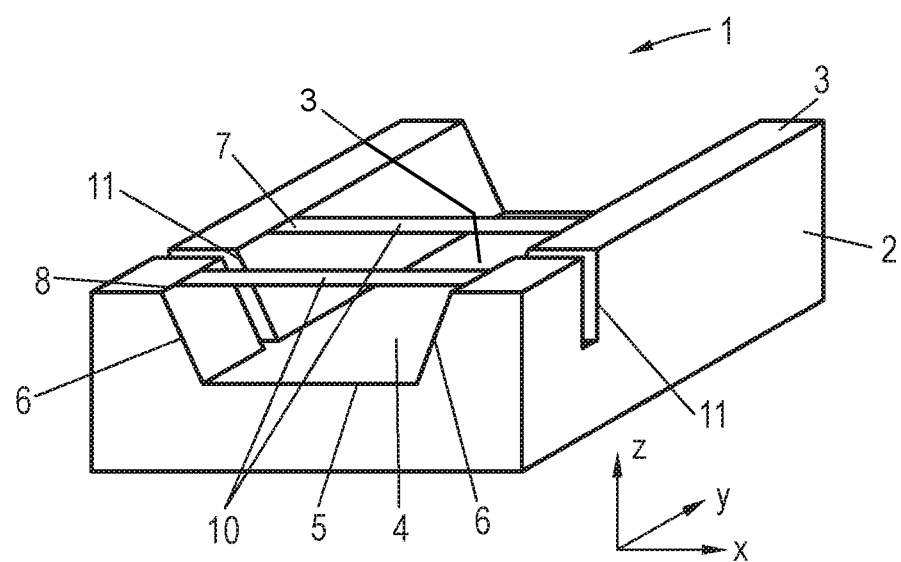
FIG. 2 is a perspective view of the first exemplary embodiment of the thermal gas sensor according to the invention.

FIG. 2 represents a schematic perspective view of the first exemplary embodiment of the thermal gas sensor 1. For the sake of clarity, only the region around the trench 4 is represented. The trapezoidal cross section of the trench 4, which is formed by the trench bottom 5 as well as the two walls 6 of the trench, can be seen. The represented web sections 10 of the conductor structures 7, 8 cross over the trench 4 in a self-supporting fashion and are respectively adjoined on both sides, as is shown in FIG. 1, by a contact section 9 (not represented in FIG. 2).

The slots 11, which cut through the surface 3 of the substrate 2 between the contact sections 9, in this exemplary embodiment have the same depth as the trench 4, and respectively cut through a wall 6 of the trench 4. The trench may in this case have a depth of between 100 µm and 500 µm. The width of the slots in the longitudinal direction of the trench 4, i.e. here in the Y direction, is for example between 1 µm and 50 µm, in particular between 10 µm and 20 µm. The trench may have a width of between 0.5 mm and 5 mm in the transverse direction, i.e. here in the X direction. By the slots 11, as can be seen here, a solid-state contact between the substrate 2 below the conductor structure 7 and the substrate 2 below the conductor structure 8 is broken at least in regions, so that in these regions no thermal conduction, or only reduced thermal conduction, can take place through the substrate. The substrate 2 consists, for example, of silicon which is coated on the surface fully or at least in regions with an insulation layer, for example of silicon nitride, in order to prevent a parasitic flow of current between the conductor structures 7, 8, to keep such a flow of current sufficiently small. The conductor structures 7, 8 may for example consist of nickel with a width, that is to say in relation to FIG. 2 with an extent in the Y direction, of between 1 µm and 20 µm, for example 10 µm, and a thickness, that is to say in relation to FIG. 2 with an extent in the Z direction, of between 50 nm and 300 nm, for example 200 nm.

For the slots 11, provision may be made for them to have a different depth than the trench 4. For example, it is possible for the slots 11 to have a smaller or a greater depth than the trench 4. As an alternative, provision may also be made for the slots 11 not to cut through the wall 6 of the trench 4, a small connecting web of the substrate 2 respectively remaining at the edge of the trench 4 in the region of the wall 6.

Figure 3:
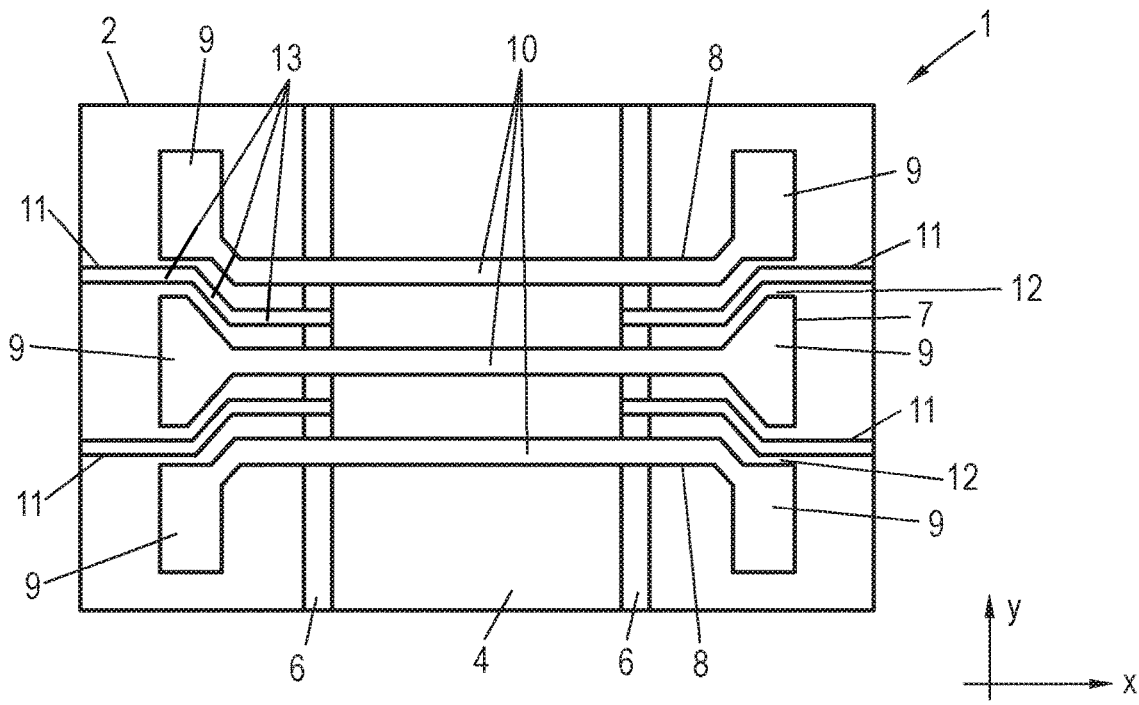
FIG. 3 is a plan view of a second exemplary embodiment of a thermal gas sensor according to the invention.

FIG. 3 represents a schematic plan view of a second exemplary embodiment of the gas sensor 1 according to the invention. In this exemplary embodiment, the conductor structure 7 as well as the two conductor structures 8 are provided, which respectively comprise a web section 10 as well as two contact sections 9 connected to the web section 10. The contact sections 9 of the conductor structures 7, 8 in this case have a different geometry than in the first exemplary embodiment presented above. The slots 11 provided between the contact sections 9 respectively extend in the region 12 of the surface 3 of the substrate 2 between two neighboring contact sections 9. The slots 11 comprise a plurality of straight sections 13 following on from one another, which respectively meet one another at an angle. This makes it possible for the slots 11, at least in sections, to follow a contour of one or both of the contact sections 9.

The regions 12 of the surface 3 of the substrate 2 between two neighboring contact sections 9 are respectively cut through centrally by the slots 11.

In this exemplary embodiment as well, the conductor structure 7 may be used as a heating element, and the two conductor structures 8, which are arranged offset in the Y direction on two sides next to the conductor structure 7, may be used as a resistance thermometer. It is of course possible for the gas sensor 1 to comprise further conductor structures 8 used as a resistance thermometer, which are respectively arranged offset at different distances in either the positive or negative Y direction relative to the conductor structure 7 used as a heating element. If further conductor structures 8 are provided, there will be a greater distance from the web section 10 of the conductor structure 7 for their web sections 10. In this way, a resistance change may be measured at different successive instants on web sections 10, located at different distances away, of the conductor structures 8.

Figure 4:
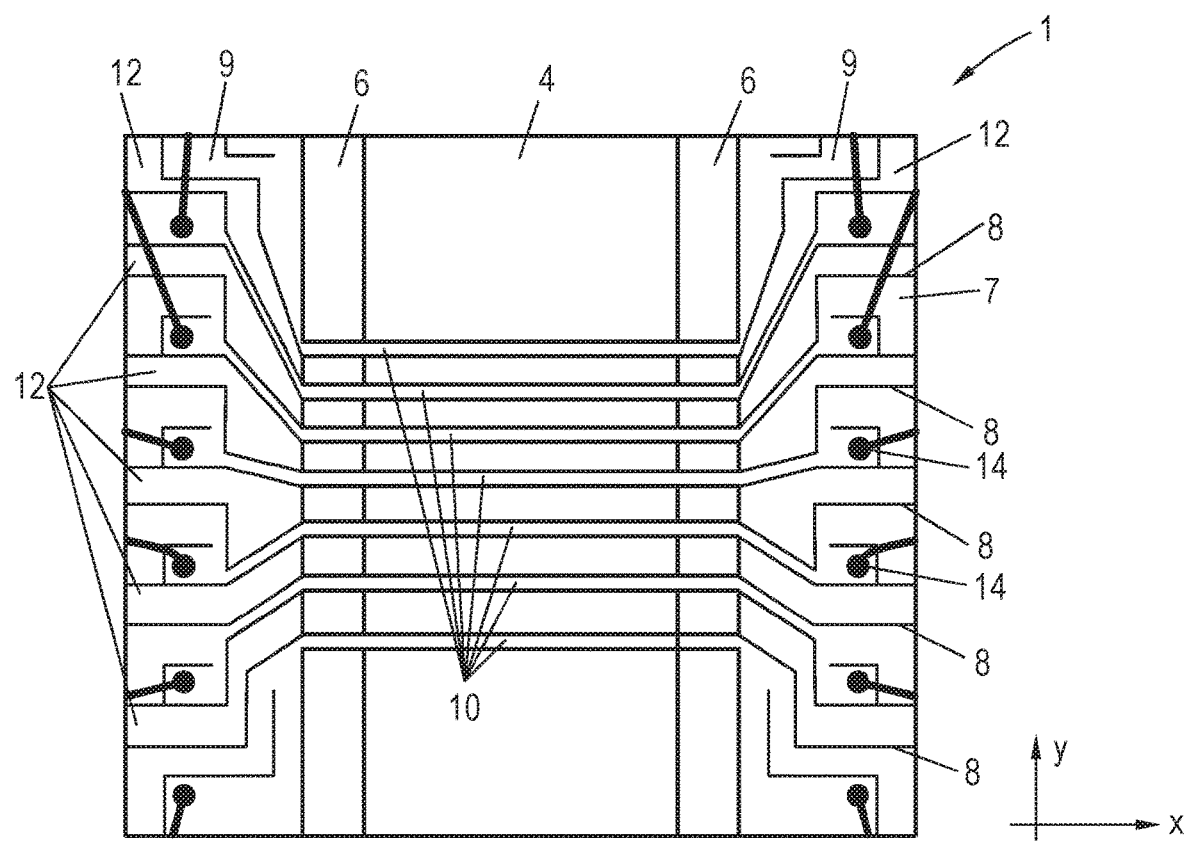
FIG. 4 is a plan view of a third exemplary embodiment of a thermal gas sensor according to the invention.

FIG. 4 represents a schematic view of a third exemplary embodiment of the gas sensor 1 according to the invention. It comprises a conductor structure 7 which has a web section 10, crossing over the trench 4, as well as two contact sections 9. Arranged offset in the positive Y direction, there is a conductor structure 8 which comprises a web section 10, crossing over the trench 4, as well as four contact sections 9, two of the contact sections 9 respectively being arranged on the two sides of the trench 4. Correspondingly, arranged in the negative Y direction from the conductor structure 7, there are five further conductor structures 8, the web sections 10 of which are arranged at different distances from the web section 10 of the conductor structure 7. These conductor structures 8 also respectively comprise four contact sections 9, of which two contact sections 9 are respectively arranged on one side of the trench 4. The arrangement of respectively two contact sections 9 for each of the conductor structures 8 on the two sides of the trench 4 makes it possible, for calibration of the gas sensor 1 at the conductor structures 8 used as a resistance thermometer, to carry out a four-point measurement in order to determine the electrical resistance of its web section 10. The distances shown for the web sections 10 are exemplary, and it is of course possible to select different distances between the web sections 10 and/or a different number of conductor structures 8. In the regions 12 between the contact sections 9, there are one or more slots 11, which are not indicated separately for the sake of clarity. Preferably, there is respectively a slot 11 at least between the contact sections 9 of the conductor structure 7 and the neighboring contact sections 9 of the conductor structures 8 on the two sides of the trench 4. Furthermore preferably, a slot 11 may respectively be provided between neighboring contact sections 9 of the conductor structures 8.

FIG. 4 furthermore represents bond contacts 14, which are respectively connected to two contact sections 9 of the conductor structures 7, 8 and via which a current can be applied to the web section 10 of the conductor structure 7, in order to heat it, or respectively via which a resistance change in the web section 10 can be measured in the case of the conductor structures 8. The bond contacts of the uppermost conductor structure 8 are not represented in this case.

A resistance measurement of the web sections 10 of the conductor structures 8 may, for example, be carried out by connecting the conductor structures 8 in a bridge circuit so that a resistance change of a web section 10, which forms the essential part of the resistance of the respective conductor structure 8, and be measured in a simple way. To this end, the gas sensor 1 may, for example, be connected by means of the bond contacts 14 to an external measuring device such as a microcontroller or the like.

A measurement of the thermal diffusivity of a gas or gas mixture surrounding the web sections 10 of the conductor structures 7, 8 by means of an exemplary embodiment of a method according to the invention may be carried out in that the web section 10 of the conductor structure 7 is heated by a current pulse, a time-dependent resistance measurement respectively being carried out on the web sections 10 of the conductor structures 8. As a function of the thermal diffusivity of the gas as well as of the distance of the respective web section 10 of the conductor structure 8 from the web section 10 of the conductor structure 7, different instants occur at which the heat coming from the heated web section 10 of the conductor structure 7 causes a resistance change of the web sections 10 of the conductor structures 8. With known distances of the web sections 10 from one another, the thermal diffusivity of the gas, or of the gas mixture, may be deduced from the time-dependent measurements. The thermal diffusivity may, for example, be used in order to determine the type of the gas and/or the nature of the composition of the gas mixture.

A measurement of the thermal conductivity of a gas or gas mixture surrounding the web sections 10 of the conductor structures 7, 8 by means of an exemplary embodiment of a method according to the invention may be carried out in that the web section 10 of the conductor structure 7 is heated by a current pulse, a temperature value respectively being measured at the web sections 10 of the conductor structures 8. As a function of the thermal conductivity of the gas, as well as of the distance of the respective web section 10 of the conductor structure 8 from the web section 10 of the conductor structure 7, different temperatures occur, to which the web sections 10 of the conductor structures 8 are heated by the heat coming from the heated web section 10 of the conductor structure 7. The temperature of the web sections 10 of the conductor structures 8 may be measured as a resistance change of the web sections 10 of the conductor structures 8.

From the temperature values which are measured at the conductor structures 8, parameters may subsequently be calculated which parameterize a best-fit line that describes the relationship between the logarithm of the distance of the respective web section 10 of one of the conductor structures 8 from the web section 10 of the heated conductor structure 7 and the temperature measurement value. The thermal conductivity of the gas or gas mixture surrounding the web sections 10 may subsequently be determined from the parameters. By the use of conductor structures 8 which are arranged at a distance from the conductor structure 7 on the two sides along the trench 4, temperature values may be obtained for different distances and/or redundant temperature values may be obtained for the same distances.

The following is a summary list of reference numerals and the corresponding structure used in the above description of the invention:

1 gas sensor
2 substrate
3 surface
4 trench
5 bottom
6 walls
7 conductor structure
8 conductor structure
9 contact section
10 web section
11 slot
12 region
13 section
14 bond contact

The invention claimed is:

1. A measuring device for measuring thermal diffusivity and/or thermal conductivity of a gas or a gas mixture, the measuring device comprising:
 a thermal gas sensor, containing:
  a substrate having a surface with a trench formed therein; and
  at least three conductor structures disposed at a distance from one another on said surface of said substrate, said conductor structures respectively having at least two contact sections and a web section connected to said contact sections, said web section of each of said conductor structures crossing over said trench at a distance from one another;
 wherein said substrate has at least one slot formed therein between said contact sections of different ones of said conductor structures in at least one region of said surface of said substrate;
 wherein the measuring device is adapted to apply a time-limited current pulse to a heated conductor structure of said at least three conductor structures of said thermal gas sensor, the measuring device configured to:
  conduct a time-dependent measurement of an electrical resistance of at least one further conductor structure of said at least three conductor structures and to determine the thermal diffusivity of the gas or the gas mixture from the time-dependent measurement of the electrical resistance of said at least one further conductor structure and a distance of web sections of said conductor structures from one another; and/or
  measure temperature values by means of at least two further conductor structures of said at least three conductor structures of said thermal gas sensor and to determine the thermal conductivity of the gas or gas mixture from the temperature values of said at least two further conductor structures as well as the distance of the web sections of said at least two further conductor structures from the web section of said heated conductor structure.

2. The measuring device according to claim 1, wherein said trench extends along a longitudinal direction of said substrate, each said web section of said conductor structures crossing over said trench parallel or essentially parallel to a transverse direction of said substrate.

3. The measuring device according to claim 1, wherein said slot contains at least one straight section, said slot fully or partially cutting into said region of said surface of said substrate between said at least two contact sections.

4. The measuring device according to claim 1, wherein said trench and/or said at least one slot is made by etching said substrate in regions.

5. The measuring device according to claim 1, wherein:
 said conductor structures are formed at least partially of nickel; and/or
 said substrate is formed at least partially of silicon and/or silicon nitride.

6. The measuring device according to claim 1, wherein said slot contains a plurality of straight sections following on from one another, said slot fully or partially cutting into said region of said surface of said substrate between said at least two contact sections.

7. The measuring device according to claim 1, wherein:
said trench has a bottom and at least two walls, said walls extending between said surface of said substrate and said bottom of said trench; and
said at least one slot extending from an upper side of said substrate to said bottom of said trench, and/or said at least one slot extending through one of said walls of said trench.

8. The measuring device according to claim 7, wherein said bottom of said trench is disposed parallel said surface of said substrate.

9. The measuring device according to claim 1, wherein:
said slot has a width of between 1 μm and 50 μm; and/or
said trench has a width of between 0.5 mm and 5 mm and/or a depth of between 100 μm and 500 μm.

10. The measuring device according to claim 9, wherein said width of said slot is between 10 μm and 20 μm.

11. The measuring device according to claim 1, wherein via said at least two contact sections, said conductor structures can be energized in order to energize said web section of said conductor structures and/or can be contacted in order to measure a resistance of said web section, at least one of said conductor structures having two further contact sections in order to measure a potential drop across said web section.

12. The measuring device according to claim 11, wherein a conductor structure of said conductor structures forms a resistance thermometer and has four said contact sections and is respectively disposed on said surface of said substrate, on two opposite sides of one of said conductor structures which forms a heating element and has two said contact sections, said slot being formed between said contact sections of said heating element and respectively at least one said contact section of said resistance thermometer.

* * * * *